(12) United States Patent
Eijkenboom

(10) Patent No.: US 8,236,355 B2
(45) Date of Patent: Aug. 7, 2012

(54) COX-2 INHIBITOR

(75) Inventor: Maria Maud L. Eijkenboom, Melville (AU)

(73) Assignee: Cambridge Scientific Pty Ltd., Leederville, Western Australia (AU)

( * ) Notice: Subject to any disclaimer, the term of this patent is extended or adjusted under 35 U.S.C. 154(b) by 630 days.

(21) Appl. No.: 12/226,786

(22) PCT Filed: Apr. 27, 2007

(86) PCT No.: PCT/AU2007/000555
§ 371 (c)(1),
(2), (4) Date: Apr. 27, 2009

(87) PCT Pub. No.: WO2007/124541
PCT Pub. Date: Nov. 8, 2007

(65) Prior Publication Data
US 2009/0221534 A1    Sep. 3, 2009

(30) Foreign Application Priority Data

Apr. 28, 2006 (AU) ................................. 2006902207
Aug. 14, 2006 (AU) ................................. 2006904367

(51) Int. Cl.
*A61K 35/16* (2006.01)
*A61K 38/40* (2006.01)
*A61K 39/00* (2006.01)
*A61K 39/38* (2006.01)

(52) U.S. Cl. .................. 424/530; 424/94.64; 424/184.1

(58) Field of Classification Search ........................ None
See application file for complete search history.

(56) References Cited

FOREIGN PATENT DOCUMENTS

WO    WO-2006/084334 A1    8/2006

OTHER PUBLICATIONS

Hawkey et al. New drug classes: COX-2 inhibitors. The Lancet, Jan. 23, 1999. vol. 353, pp. 307-314.*
Scopes R.K., "Protein Purification", Principles and Practice 3rd Edn, Springer-Verlag. USA 1994, Chp 4; pp. 71-101.

* cited by examiner

*Primary Examiner* — Marcela M Cordero Garcia
(74) *Attorney, Agent, or Firm* — Edwards Wildman Palmer LLP; Jeffrey D. Hsi

(57) ABSTRACT

The present invention relates to an agent having COX-2 inhibition activity. In particular the present invention relates to a COX-2 inhibitor separated from a mixture of denatured plasma and at least one metal, metal ion or metal salt thereof.

19 Claims, 6 Drawing Sheets

COX-2 INHIBITOR

CROSS-REFERENCE TO RELATED APPLICATIONS

This application is the National Stage of PCT/AU2007/000555, filed Apr. 27, 2007, which claims benefit of Australian Application 2006902207, filed Apr. 28, 2006 and 2006904367, filed Aug. 14, 2006. The entire contents of each of these applications is incorporated herein by reference.

FIELD

The present invention relates to an agent having COX-2 inhibition activity. In particular the present invention relates to a composition comprising an effective amount of a COX-2 inhibitor separated from a mixture of plasma and at least one metal, metal ion or metal salt thereof, wherein said mixture has been denatured.

BACKGROUND

COX-2 inhibitors are newly developed drugs for inflammation that block the COX-2 enzyme. Blocking this enzyme impedes the production of prostaglandins that cause the pain and swelling of arthritis inflammation. While COX-2 inhibitors are classified as non-steroidal anti-inflammatory drugs (NSAIDs), most do not have the same problems as other NSAIDs, as they generally block the COX-2 enzyme and not the COX-1 enzyme.

Common examples of NSAIDs which affect both the COX-1 and COX-2 enzymes include aspirin, indomethacin (Indocin), ibuprofen (Motrin), naproxen (Naprosyn), piroxicam (Feldene), and nabumetone (Relafen). These drugs are commonly prescribed medications for the inflammation of arthritis and other body tissues, such as in tendinitis and bursitis. However, all of these medications have side effects. The major common side effects of these NSAIDs are related to the gastrointestinal system. Some 10%-50% of patients are unable to tolerate NSAID treatment because of side effects, including abdominal pain, diarrhea, bloating, heartburn, and dyspepsia. Approximately 15% of patients on long-term NSAID treatment develop ulceration of the stomach and duodenum. Even though many of these patients with ulcers do not have symptoms and are unaware of their ulcers, they are at risk of developing serious ulcer complications such as bleeding or perforation of the stomach.

The annual risk of serious complications with chronic NSAID use is 1%-4%. The risk of complications is higher in elderly patients, rheumatoid arthritis sufferers, patients on anticoagulants such as Coumadin and heparin or cortisone medication, and patients with heart disease or a prior history of bleeding ulcers.

Cyclooxygenase-1 (COX-1) is an enzyme which is normally present in a variety of areas of the body, including sites of inflammation and the stomach. The COX-1 enzyme of the stomach produces prostaglandins that ensure the natural mucus lining which protects the inner stomach. Common anti-inflammatory drugs like aspirin block the function of the COX-1 enzyme along with COX-2. When the COX-1 enzyme is blocked, inflammation is reduced, but the protective mucus lining of the stomach is also reduced, which can cause stomach upset, ulceration, and bleeding from the stomach and intestines.

Cyclooxygenase-2 (COX-2) produces prostaglandins, but the COX-2 enzyme is located specifically in areas of the body that are responsible for inflammation and not in the stomach. When the COX-2 enzyme is blocked, inflammation is reduced. Since the COX-2 enzyme does not play a role in the normal function of the stomach or intestinal tract, medications which selectively block COX-2 do not present the same risk of injuring the stomach or intestines.

Accordingly, the development of new COX-2 inhibitors is desirable as COX-2 inhibitors provide the benefits of reducing inflammation without irritating the stomach.

SUMMARY

The inventors have surprisingly identified a new COX-2 inhibitor in plasma. Accordingly, in a first aspect, the present invention provides a composition comprising an effective amount of a COX-2 inhibitor separated from a mixture of denatured plasma and at least one metal, metal ion or metal salt thereof.

The plasma may be obtained from any animal source. Preferably, the plasma is isolated from an animal selected from the group consisting of human, equine, bovine, ovine, murine, caprine and canine.

Once the plasma is isolated it is manufactured to form the COX-2 inhibitor. Accordingly, in a second aspect, the present invention provides a method of manufacturing a COX-2 inhibitor comprising:
(a) mixing plasma with sodium bicarbonate ($NHCO_3$) and incubating said mixture for sufficient time and at a temperature of no more than 80° to produce a precipitate;
(b) resolubilising said precipitate in the presence of an aqueous solution at a temperature of between about 80° C. and about 150° C., wherein either before, during or after the resolubilising step at least one metal, metal ion or metal salt thereof is admixed; and
(c) separating a COX-2 inhibitor fraction from the resolubilised precipitate in step (b), which fraction comprises denatured plasma proteins and at least one metal, metal ion or metal salt thereof.

In some embodiments, a protease such as trypsin is added in step (a) or step (b) in order to further enhance denaturation. The protease may be added before or after heating the mixture.

In some embodiments, the step of separating the COX-2 inhibitor is by chromatography such as affinity chromatography, column chromatography, partition chromatography, gel-filtration chromatography with a suitable solvent or solvent mixture.

The plasma may be obtained from any animal source. Preferably, the plasma is isolated from an animal selected from the group consisting of human, equine, bovine, ovine, murine, caprine and canine.

The metal, metal ion or metal salt thereof can be any metal. In some embodiments, the metal is selected from the group consisting of nickel, sodium, copper, zinc, cobalt, iron, magnesium, manganese, potassium, silver and mercury, ions or salts thereof and mixtures thereof.

The first heating step (step a) is carried out at no more than 80° C. Preferably, the temperature is between 50° C. and 80° C. More preferably, the temperature is between 60° C. and 70° C. Most preferably, the temperature is about 65° C.

The second heating step (step b) is carried out between about 80° C. and about 150° C. In some embodiments the second heating step is carried out between about 90° C. and about 130° C. In some embodiments the second heating step is carried out at about 120° C. to produce a solubilised precipitate comprising denatured proteins having COX-2 inhibitor activity.

The mixture can be used directly or further separated to produce a fraction having COX-2 inhibitor activity.

In a second aspect, the present invention provides a composition comprising a fraction of denatured plasma proteins and at least one metal, metal ion or metal salt thereof, wherein said mixture has COX-2 inhibitor activity.

In some embodiments, the composition of the invention comprises at least a fraction of a mixture as described above. In some embodiments, the composition of the invention is admixed with a pharmaceutical carrier. Any pharmaceutical carrier known in the art may be used.

In a third aspect the present invention provides a composition having COX-2 inhibitor activity obtained by:
(a) mixing plasma with sodium bicarbonate ($NHCO_3$) and protease and incubating said mixture for sufficient time and at a temperature of no more than 80° to produce a precipitate;
(b) resolubilising said precipitate in the presence of an aqueous solution at a temperature of between about 80° C. and about 150° C., wherein either before, during or after the resolubilising step at least one metal, metal ion or metal salt thereof is admixed; and
(c) separating a COX-2 inhibitor fraction from the resolubilised precipitate in step (b), which fraction comprises denatured plasma proteins and at least one metal, metal ion or metal salt thereof.

In some embodiments, the step of separating the COX-2 inhibitor fraction is by chromatography such as affinity chromatography, column chromatography, partition chromatography, gel-filtration chromatography with a suitable solvent or solvent mixture.

In a fourth aspect, the present invention provides a method for mediating COX-2 levels in a subject, said method comprising administering to the subject an effective amount of a composition comprising a fraction of denatured plasma proteins and at least one metal, metal ion or metal salt thereof.

The method of administration may be any method known in the art. The composition may be administered topically, systemically, intramuscularly, subcutaneously, intraperitoneally, intrapleurally, intraarticularly, intrathecally, rectally, vaginally, or by inhalation. In some embodiments the composition is administered topically.

In a fifth aspect, the invention provides a composition for mediating COX-2 levels in a subject, comprising a pharmaceutically acceptable carrier and an effective amount of a composition comprising a fraction of denatured plasma proteins and at least one metal, metal ion or metal salt thereof.

In a sixth aspect, the invention provides a physiologically active substance which is extracted from a mixture of plasma and at least one metal, metal ion or metal salt thereof, wherein said mixture has been denatured.

In some embodiments the physiologically active substance is further admixed with a pharmaceutically acceptable carrier. Preferably, the carrier is at least one member selected from the group consisting of distilled water, physiologically saline solution, Ringer's solution, plant oil, synthetic fatty acid glycerides, higher fatty acid esters, propylene glycol, lactose, mannitol, corn starch, crystalline cellulose, gum arabicum, gelatin, potato starch, carmerose, carmerose calcium, talc, and magnesium stearate.

In a seventh aspect, the invention provides a method for treating a COX-2 mediated disease or disorder, comprising administering a fraction having COX-2 inhibitor activity and separated from a mixture of plasma and at least one metal, metal ion or salt thereof, wherein said mixture has been denatured and wherein said fraction is admixed with a pharmaceutically acceptable carrier.

In an eighth aspect, the invention provides use of a composition made by the method of the first aspect in the manufacture of an agent used to treat a disease or disorder associated with aberrant COX-2 activity.

In a ninth aspect, the present invention provides a method for treating a subject afflicted with inflammation comprising administering an effective amount of a COX-2 inhibitor fraction separated from a mixture of denatured plasma and at least one metal, metal ion or salt thereof, wherein said fraction is admixed with a pharmaceutically acceptable carrier.

In a tenth aspect the present invention provides a COX-2 inhibitor composition comprising an effective amount of soluble plasma consisting essentially, of protein or protein fragments isolated from plasma, wherein said protein or protein fragments have molecular weights less than 50 kDa as determined by SDS-PAGE.

BRIEF DESCRIPTION OF THE FIGURES

FIG. 3 (right panel) shows a 12% SDS-PAGE Tricine gel. Proteins were silver-stained Lane 5 contains molecular weight markers. Lane 6 shows untreated bovine plasma. This gel shows that the the majority of proteins in unpurified bovine plasma are in a size range of 50-80 kilodaltons.

Figure 1:
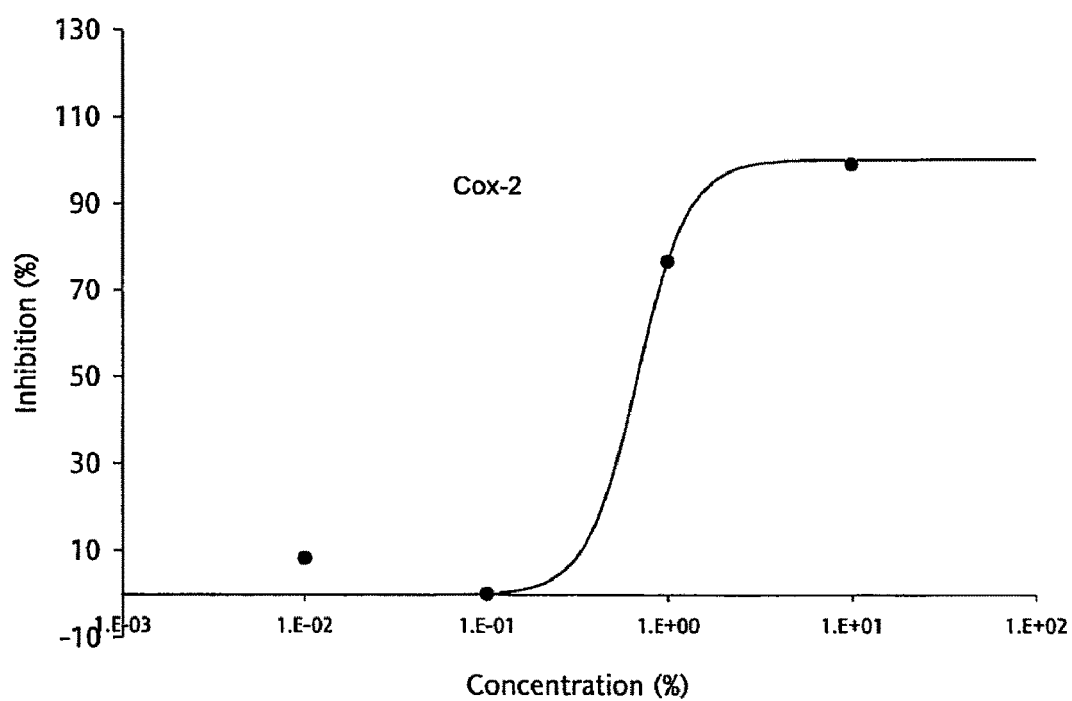
FIG. 1 shows a dose response curve for % inhibition of COX-2 activity by the COX-2 inhibitor of the present invention.

DESCRIPTION OF THE INVENTIONS
PREFERRED EMBODIMENTS

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional chemistry and pharmacology within the skill of the art. Such techniques are well known to the skilled worker, and are explained fully in the literature. See, eg., Coligan, Dunn, Ploegh, Speicher and Wingfield "Current protocols in Protein Science" (1999) Volume I and II (John Wiley & Sons Inc.); The Merck Index, 12th Edition (1996), Therapeutic Category and Biological Activity Index; and Remington's Pharmaceutical Sciences, 17$^{th}$ Edition, Mack Publishing Company, Easton, Pa., USA.

It must be noted that as used herein and in the appended claims, the singular forms "a," "an," and "the" include plural reference unless the context clearly dictates otherwise. Thus, for example, a reference to "a metal" includes a plurality of such metals, and a reference to "an isolated protein" is a reference to one or more proteins, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In its broadest aspect, the present invention provides a composition useful as a COX-2 inhibitor.

It will be appreciated that the term "COX-2 inhibitor" reflects compounds and compositions of the present invention that are capable of blocking or reducing the activity or function of the cyclooxygenase-2 (COX-2) enzyme. Specifically, by reducing or blocking the COX-2 enzyme, the COX-2 inhibitor of the present invention is capable of providing anti-inflammatory activity.

The term "anti-inflammatory" is intended to include an inflammatory response modifier, including all inflammatory responses such as production of stress proteins, white blood cell infiltration, fever, pain, swelling and so forth.

The composition of the present invention will therefore be administered as an effective amount to a subject in need of anti-inflammatory treatment. The term "effective amount" refers to that amount which is sufficient to induce or maintain an anti-inflammatory effect. What constitutes an effective inflammatory amount, or dose, of the composition of the present invention depends, among other factors, on the body weight of the subject and the intensity of the inflammation being treated. Normally an effective dose will be found in the range of about 1 to about 6 mg/kg body weight. For an average 75 kg subject, this range equates to a dose of about 75 to about 450 mg. Proportionately smaller or larger doses can be appropriate for subjects having lesser or greater body weight. Such a dose can be administered as needed, but typically administration 1 to about 4 times per day, in most cases 1 or 2 times a day, provides adequate continuing relief of pain.

The COX-2 inhibitor composition of the present invention essentially comprises a mixture of denatured plasma protein and at least one metal, metal ion or metal salt.

In some embodiments, the COX-2 inhibitor composition of the present invention essentially comprises a mixture of denatured plasma protein and at least one metal, metal ion or metal salt, wherein said protein or protein fragments have molecular weights less than 50 kDa as determined by SDS-PAGE.

The term "plasma" are used herein typically refers to the straw-coloured fluid in which the blood cells are suspended. It consists of various inorganic salts of sodium, potassium, calcium etc. with a high concentration of protein (approximately 70 g/l) and a variety of trace elements.

The plasma used in the present invention may be obtained from any animal source as plasma can be prepared from the blood of any animal. In some embodiments, the plasma is isolated from blood taken from an animal selected from the group consisting of human, equine, bovine, ovine, murine, caprine and canine. In some embodiments, the animal source for the plasma is bovine.

The plasma may be freshly isolated or lyophilised. In some embodiments, blood is isolated from cattle and the haemoglobin is removed by standard procedures. The plasma is then mixed with sodium bicarbonate (approx. 20 g per liter) and heated to no more than 80° C. for at least 30 minutes or until the coagulated plasma proteins precipitate. The precipitate is then isolated and used directly or lyophilised by standard procedures for further use.

In some embodiments, a protease selected from the group consisting of trypsin, chymotrypsin, factor Xa, venom-protease, thrombin, plasmin and a serine-protease of the subtilisin family is added before heating or after heating to about 80° C. In some embodiments the protease is trypsin.

The precipitate is then resolubilised by mixing the precipitate or the lyophilised precipitate with water or other aqueous solutions (approximately 50 g per liter) and heating the mixture (second heating step) at between about 80° C. and about 150° C. In some embodiments the second heating step is carried out between about 90° C. and about 130° C. In some embodiments the second heating step is carried out at about 120° C.

At this stage i.e. before, after or during the resolubilisation step at least one metal, metal ion or salt thereof is added to the resolubilised plasma proteins. Various metals and/or metal ions are useful in the composition of the present invention and as such the present invention embraces all such metals or metal ions.

In some embodiments, the metals are selected from the group consisting of nickel, sodium, copper, zinc, cobalt, iron, magnesium, manganese, potassium, silver and mercury.

In cases where the metals are sufficiently basic or acidic to form stable non-toxic acid or base salts, the use of the metals as salts can be appropriate. Examples of acceptable metal salts include acetate, ascorbate, benzoate, bicarbonate, chloride, citrate, carbonate, α-glycerophosphate, α-ketoglutarate, malonate, methanesulfonate, nitrate, succinate, sulfate, tartarate and tosylate salts.

Metal salts can be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts can be made.

For example, the metal may be silver (I), wherein the nitrate salt provides adequate free silver (I) ion to provide the necessary metal requirement. The chloride salt on the other hand provides less silver, being less soluble and with a low dissociation constant and therefore is less useful in the invention. The skilled artisan will be able to readily determine the suitable salt form of the metal ion that provides the necessary properties for the present invention. Furthermore, the skilled artisan will be aware of the compatibility of the salt forms of the metal(s) and other components of the composition to maintain adequate levels of the metal ion(s).

In some embodiments, the metals used in the composition comprise a mixture of a number of metals. For example, the mixture of metals could consist essentially of $NiSO_4 \cdot 7H_2O$, $NH_4VO_3$, NaF, $CuSO_4.5H_2O$, $ZnCl_2$, $(NH_4)_6Mo_7O_{24}.4H_2O$, $CoCl_2.6H_2O$, $FeSO_4.7H_2O$, $MgSO_4.7H_2O$, $H_3BO_3$, $MnCl_2.4H_2O$ and $K_2CrO_4$.

Once the resolubilised plasma protein mixture comprising denatured plasma proteins and metal, metal ion or salts thereof has been obtained it can be either used directly or fractionated to obtain a more refined fraction having cytokine mediating activity. Techniques for fractionating protein-containing mixtures are well known in the art. See, for example, "Plasma Protein Fractionation" Heide K, Haupt H & Schwick H; in The Plasma Proteins, 2nd Edition Vol 3 (1977) Putnam F. (Ed); U.S. Pat. No. 4,351,710 and U.S. Pat. No. 4,322,275 both entitled "Fractionation of protein mixtures"; U.S. Pat. No. 5,138,034 entitled "Method of fractionating plasma proteins" all incorporated herein by reference.

As described above, in some embodiments, the present invention provides a method of relieving COX-2 related or mediated disease or disorder such as inflammation in a subject, the method comprising administering to the subject an effective amount of a composition of the present invention.

In some embodiments, the method of the invention can be used to relieve mild to severe, acute or chronic inflammation. The method of the invention is useful for treatment of non-human mammalian subjects or patients, including domestic, farm and exotic animals, such as for example dogs horses, zoo animals and the like, but is primarily useful for treatment of human subjects or patients.

Generally, the terms "treating," "treatment" and the like are used herein to mean affecting an individual or subject, their tissue or cells to obtain a desired pharmacological and/or physiological effect. The effect may be prophylactic in terms of completely or partially preventing the COX-2 mediated disease or sign or symptom thereof, and/or may be therapeutic in terms of a partial or complete cure of the COX-2 mediated disease. "Treating" as used herein covers any treatment of, or prevention of inflammation in a vertebrate, a mammal, particularly a human, and includes: (a) preventing the COX-2 mediated disease from occurring in a subject that may be predisposed to the COX-2 mediated disease, but has not yet occurred; (b) inhibiting the COX-2 mediated disease, i.e., arresting its development; or (c) relieving or ameliorating the symptoms of the COX-2 mediated disease, i.e., cause regression of the symptoms of the COX-2 mediated disease.

While the methods of the present invention are primarily directed towards inflammation the compositions of the present invention are also useful in the treatment and/or prevention of a wide range of conditions and disorders mediated by COX-2, including but not restricted to disorders characterized by inflammation, pain and/or fever. Such compositions are especially useful as anti-inflammatory agents, such as in treatment of arthritis. In particular, such compositions have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions useful in methods of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Such compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Compositions of the present invention can also be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise a composition useful in methods of the invention with one or more compounds selected from aceclofenac, acemetacin, α-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see The Merck Index, 12th Edition (1996), Therapeutic Category and Biological Activity Index, lists therein headed "Analgesic", "Anti-inflammatory" and "Antipyretic").

Still other suitable formulations for use in the present invention can be found in Remington's Pharmaceutical Sciences, Mace Publishing Company, Philadelphia, Pa. 17th ed. (1985).

The terms "administration," administering," and "administered" are used herein interchangeably. The COX-2 inhibitor composition of the present invention may be administered orally including sublingual, topically, or parenterally in dosage unit formulations containing conventional non-toxic pharmaceutically acceptable carriers, adjuvants, and vehicles. The term "parenteral" as used herein includes subcutaneous injections, aerosol, intravenous, intramuscular, intrathecal, intracranial, injection or infusion techniques or rectal or vaginally. Preferably, the COX-2 inhibitor composition of the present invention is administered together with a pharmaceutically acceptable carrier or diluent compatible with the composition. In preparing such composition, any conventional pharmaceutically acceptable carrier can be utilised.

The carrier material can be organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutically active preparations may contain other pharmaceutically active agents. Additionally, additives such as flavouring agents, preservatives, stabilisers, emulsifying agents, buffers and the like may be added in accordance with accepted practices of pharmaceutical compounding.

When the COX-2 inhibitor composition of the present invention is administered orally, it is generally administered at regular intervals, conveniently at meal times or once daily. The COX-2 inhibitor composition of the present invention can be made up in any conventional form including: (a) solid form for oral, rectal or vaginal administration such as tablets, capsules (eg. hard or soft gelatine capsules), pills, sachets, powders, granules, and the like; and (b) preparations for topical administrations such as solutions, suspensions, ointments, creams, gels, micronised powders, sprays, aerosols and the like; (c) liquid formulations for intravenous administrated may also be prepared. Pharmaceutical preparations may be sterilised and/or may contain preservatives, stabilisers, wetting agents, emulsifiers, salts for varying the osmotic pressure and/or buffers.

For topical administration to the skin or mucous membrane the aforementioned COX-2 inhibitor composition of the present invention is preferably prepared as an ointment, tincture, cream, gel, solution, lotion, spray; aerosol and dry powder for inhalation, suspension and the like. In fact, any conventional methods of preparing topical compositions can be utilised in this invention. Among the preferred methods of applying the COX-2 inhibitor composition of the present invention is in the form of an ointment, gel, cream, lotion, spray; aerosol or dry powder for inhalation. A pharmaceutical preparation for topical administration to the skin can be prepared by mixing the COX-2 inhibitor composition of the present invention with non-toxic, therapeutically inert, solid or liquid carriers customarily used in such preparation. These preparations generally contain 0.01 to 5.0 percent by weight, preferably 0.1 to 1.0 percent by weight, of the COX-2 inhibitor composition of the present invention, based on the total weight of the peptide preparation.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the afore-mentioned active agent. Among the conventional antioxidants which can be utilised in these preparations are included N-methyl-α-tocopherolamine, tocopherols, butylated hydroxyanisole, butylated hydroxytoluene, ethoxyquin and the like. Cream-base pharmaceutical formulations containing the antigen preparation, used in accordance with this invention, are composed of aqueous emulsions containing a fatty acid alcohol, semi-solid petroleum hydrocarbon, ethylene glycol and an emulsifying agent.

Ointment formulations containing the COX-2 inhibitor composition of the present invention comprise admixtures of a semi-solid petroleum hydrocarbon with a solvent dispersion of the analgesic and/or anti-inflammatory composition. Cream compositions containing the COX-2 inhibitor composition of this invention preferably comprise emulsions formed from a water phase of a humectant, a viscosity stabiliser and water, an oil phase of a fatty acid alcohol, a semi-solid petroleum hydrocarbon and an emulsifying agent and a phase containing COX-2 inhibitor composition dispersed in an aqueous stabiliser-buffer solution. Stabilisers may be added to the topical preparation. Any conventional stabiliser can be utilised in accordance with this invention. In the oil phase, fatty acid alcohol components function as a stabiliser. These fatty acid alcohol components function as a stabiliser. These fatty acid alcohol components are derived from the reduction of a long-chain saturated fatty acid containing at least 14 carbon atoms.

Formulations for aerosols are described in Drugs and Pharmaceutical Sciences, Marcel Dekker, New York, 72: 547-574 (1996). Furthermore, the COX-2 inhibitor composition of the present invention can be delivered by dry powder inhalation. Such formulations and devices are described in Pharmaceutical Technology, June 1997, pp. 117-125.

Depending upon the mode or type of administration and the severity of the inflammation, the treatment regime will vary. However, typically an individual is monitored hourly or daily, depending on the above factors, and the status of inflammation is determined. Administration of the COX-2 inhibitor composition of the present invention continue until the inflammation is reduced or alleviated.

Protocols for conducting human pharmacokinetic studies are well known in the art and any standard protocol can be used to determine whether a particular composition of the present invention satisfies the pharmacokinetic criteria set out herein. An example of a suitable protocol is described below.

In some embodiments, the compositions of the present invention, upon administration, reduce the activity of the COX-2 enzyme present in an individual's tissue as compared to untreated tissue. Accordingly, the present invention encompasses a method of reducing the activity of COX-2 enzyme in an individual's tissue comprising the step of administering an effective amount of a COX-2 inhibitor composition comprising an effective amount of a COX-2 inhibitor active fraction separated from a mixture of denatured plasma and at least one metal, metal ion or metal salt thereof, wherein the composition reduces the activity of COX-2 enzyme in the individual's tissue compared to untreated tissue.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention will now be further described by way of reference only to the following non-limiting examples. It should be understood, however, that the examples following are illustrative only, and should not be taken in any way as a restriction on the generality of the invention described above. In particular, while the invention is described in detail in relation to the use of specific animal plasma and metals, it will be clearly understood that the findings herein are not limited to these ingredients.

Example 1

Preparation of Cox-2 Inhibitor Composition 200 liters of sterile cattle blood was centrifuged at 1000-1300×g for 10 minutes and the haemoglobin was removed from the plasma. After centrifugation approximately 100 liters of plasma was gained, and transferred into a dish, suitable for heating and continuous mixing. To the plasma liquid 2 kg Sodium Bicarbonate ($NaHCO_3$) was added and mixed until the $NaHCO_3$ dissolved, then the solution was heated to 80° C. Denatured plasma protein was then recovered and placed on filter paper to dry. The solid sediment was then pressed to produce a 60 kg solid plasma-protein "block" which was then lyophilised by standard procedures. After this process the plasma-protein weighed approximately 8 kg and was used in the preparation of the COX-2 inhibitor preparation as described below.

A solution was then prepared comprising 152 liters of water, 8 kg dried plasma-protein as prepared above and 200 ml of a metal-containing solution. The constituents of the metal-containing solution are shown in Table 1.

TABLE 1

| METAL-CONTAINING SOLUTION | |
|---|---|
| $NiSO_4 7H_2O$ | 10.4 g/l |
| $NH_4VO_3$ | 1.2 g/l |
| NaF | 24.0 g/l |
| $CuSO_4 \cdot 5H_2O$ | 20.0 g/l |
| $ZnCl_2$ | 47.0 g/l |
| $(NH_4)_6Mo_7O_{24} 4H_2O$ | 7.0 g/l |
| $CoCl_2 \cdot 6H_2O$ | 20.0 g/l |
| $FeSO_4 \cdot 7H_2O$ | 100.0 g/l |
| $MgSO_4 \cdot 7H_2O$ | 80.0 g/l |
| $H_3BO_3$ | 23.0 g/l |
| Glucose | 50.0 g/l |
| $MnCl_2 \cdot 4H_2O$ | 36.4 g/l |
| $K_2CrO_4$ | 1.0 g/l |
| Glycine | 75.0 g/l |
| Citric Acid | 20.0 g/l |

Made up in a 200 ml solution with water, which was then stirred for at least 20 minutes.

The mixture was then heated up to 120° C. and maintained for two hours with constant mixing. During this time the plasma-protein dissolved and was sterilized. The resulting material was then held at a temperature of about 35° C. and 0.125 g/l of trypsin was added. The material was then allowed to incubate for approximately 2 hours. The digested material was then autoclaved and cooled to produce the COX-2 inhibitor composition of the present invention.

Example 2

Manufacture of a Topical Cox-2 Inhibitor Composition

A composition comprising the ingredients shown in Table 2 were mixed at 75-80° C. in a 250 liter vacuum homogenizer equipped with anchor and turbo mixers. Then the ingredients shown in Table 3 were added and the mixing was continued at 80-83° C. for 10 minutes with the aid of the turbo mixer.

A slow cooling process was then carried out using the anchor mixer. When the material reached 60° C., the vacuum was switched on until the end of the cooling.

At 40-45° C. the ingredients shown in Table 4 were added and mixed for 10 minutes. Mixing with the anchor mixer was continued until the mixture reached 25° C.

After a standing period of approximately 24 hours, the topical COX-2 inhibitor was ready for use.

TABLE 2

| Item No. | Amount Per Kg | Ingredients |
|---|---|---|
| 1 | 20 g | Liposorb S20 (Tween 60) |
| 2 | 20 g | Cremaphor A6 |
| 3 | 10 g | Hydromyristenol |
| 4 | 40 g | Cetyl alcohol |
| 5 | 70 g | Corn Oil (Cold Pressed) |
| 6 | 30 g | Wheat Germ Oil |
| 7 | 0.24 g | Carrot Oil |
| 8 | 50 g | Isopropyl Myristate |
| 9 | 0.2 g | Butylated Hydroxytoluene B.P. |
| 10 | 3 g | Phenonip |

TABLE 3

| 11 | 400 g | Plasma protein from Example 1 |
| 12 | 15 g | Propylene Glycol B.P. |
| 13 | 15 g | Hygroplex HHG |
| 14 | 2 g | Allantoin |
| 15 | 208 g | Purified Water B.P. |
| 16 | 10 g | Germaben II |
| 17 | 4 g | Veegum |
| 18 | 100 g | Purified Water B.P. |
| 19 | 0.04 ml | Potassium Bromide 50 g/l |
| 20 | 30.7 mg | Sodium Sulphide |
| 21 | 0.04 ml | Potassium Iodide 25 g/l |

TABLE 4

| 22 | 1.4 g | Chammomile Fragrence |

Methodology

1). Add items 1 to 10 in a 250 liter steam pan and heat 75° C.;

2). Boil items 15 and 18 in the 150 liter pan and transfer 13 liters to the 50 liter pan and add Veegum and mix until homogeneous;

3). Add item 14 to the remainder of the Purified Water B.P. in the 150 liter steam pan at above 90° C. and mix. When dissolved add the items 12, 13 and 16 and maintain temperature at 75° C. with continual mixing;

4). Add the water phase (step 5) to the oil phase (step 3) and mix using a short shaft air mixer. Then add step 4 to this using a plastic sieve to ensure that no lumps are incorporated;

5). Add plasma protein from Example 1 and emulsify for 20 minutes, then continue stirring whilst water cooling to 40° C.;

6). Add items 19 to 21 allowing a few minutes in between each addition whilst mixing. Cool to below 30° C.

Example 3

Clinical Trial on Topical Cox-2 Inhibitor Composition

Twenty-three (23) randomly selected patients in a general practice setting were supplied with a preparation produced according to Example 2 above. The patients we advised to apply the preparation topically three times daily.

Patients were reviewed at regular intervals and divided into two groups:

Group A—work or injury induced conditions either acute or sub-acute eg repetitive strain injury (RSI), tennis elbow, joint and musculo-tendinous injury;

Group B—Arthritic and aging conditions—sub-acute and chronic eg osteoarthritis.

Table 5 shows the effect of using the topical composition over a three (3) month period.

TABLE 5

| Patient Details | Complaint | Result | Comments |
|---|---|---|---|
| Male - Aged 52 | Lateral epicondylitis | Improved | Full recovery |
| Male - Aged 28 | Musculo-tendinous | Full recovery | Acute soft tissue injury |
| Female - Aged 33 | Cervical soft tissue injury | Improved | Recovery after 1 week |

TABLE 5-continued

| Patient Details | Complaint | Result | Comments |
|---|---|---|---|
| Female - Aged 38 | RSI | Partial improvement | Rapid improvement, but relapse after cessation of treatment |
| Female - Aged 41 | RSI | No benefit | Poor patient selection - no treatment has worked |
| Female - Aged 64 | Reputed disc | No benefit | Pathology not treatable using analgesics/anti-inflammatory agents |
| Male - Aged 30 | Soft tissue injury | Improved | Soft tissue injury |
| Female - Aged 36 | RSI | No benefit | Too greater area to be treated with a topical agent |
| Female - Aged 50 | Lateral epicondylitis | Improved | Non-repetitive injury - Unsuccessfully treated with physiotherapy/anti-inflammatory agent |
| Female - Aged 68 | Arthritis | Improved | Pain relief but movement still restricted |
| Male - Aged 47 | Soft tissue injury | Improved | Rapid improvement, but relapse after cessation of treatment |
| Female - Aged 48 | Cervical soft tissue injury | Partial improvement | Poor compliance |
| Male - Aged 60 | Arthritis | Improved | Rapid improvement, but relapse after cessation of treatment. Intra-articular cortisone not effective |
| Female - Aged 70 | Arthritis | Improved | Rapid pain relief obtained |
| Male - Aged 68 | Arthritis | Improved | Rapid improvement, but relapse after cessation of treatment. |
| Female - Aged 56 | Arthritis | Improved | Pain relief obtained |
| Female - Aged 49 | Gout | Improved | Pain relief obtained |
| Female - Aged 80 | Calcaneal spur | No benefit | Condition not treatable with topical agent |
| Female - Aged 79 | Arthritis | Pain relief | Pain relief obtained |
| Female - Aged 69 | Arthritis | No benefit | Non-specific arthritis |
| Male - Aged 73 | Arthritis | No benefit | Poor patient selection |
| Male - Aged 67 | Inflammation | No benefit | Topical application not effective for this rheumatoid arthritis-like condition |
| Female - Aged 63 | Arthritis | No benefit | Multiple pathologies |

While these data are more qualitative than quantitative, it is readily apparent that use of the topical COX-2 inhibitor composition produced effect.

It was observed that in the more chronic situation, elderly, local arthritis (in particular osteo-arthritis), results were more predictable. Clinically, it appears that local application of the topical COX-2 inhibitor to a pathological joint produces some effect. This may in some way be related to the "massage" effect, and focusing attention of the positive aspects of treatment.

One of the most important aspects of the trial was selection of patient. Inventors believe that the nature of condition to be treated has an affect on the ability of a topical agent to work effectively. Of the small numbers used in this trial, the best results were obtained with patients having single joint pain or relatively localized non-joint pain. A patient whose general health was reasonable was more important than the age of patient. Finally, non-weight bearing joints responded more quickly than weight bearing joints.

Of the patients in Group A (acute and sub-acute), the best results were obtained where local rather than vague general inflammation was evident. Repetitive strain injury was not helped by the use of the COX-2 inhibitor unless the condition was of the very local category—eg. Tennis-elbow. Conversely, with the "arthritic" Group B pain from osteo-arthritis was definitely reduced whilst the COX-2 inhibitor was being used. However, following cessation of treatment in may instance, the inflammation gradually returned.

Example 4

Treatment of Osteoarthritis in Randomized Double Blind Study

Without wishing to be bound by any particular hypothesis or theory, the inventors believe that the active agents within the COX-2 inhibitor compositions of the present invention are metallo-peptide complexes. When used topically this preparation has been shown to be as effective as orally administered indocid (Indomethacin), a NSAID which reduces pain, swelling, and inflammation or phenylbutazone, a NSAID used in the treatment of pain, lameness, laminitis and osteoarthritis, in an animal model of inflammatory arthritis. The animal model was inflammation caused by an injection of mycobacteria into the foot pads of Long-Evans rats (data not shown).

In has also been demonstrated that the composition described in Example 2 possessed inhibitory activity against the serine proteinases-trypsin and human granulocyte elastase (HGE). Since HGE has been implicated in the destruction of cartilage in inflammatory arthritis the inhibitory properties of the composition in Example 2 against this or similar enzymes may contribute to its overall biological activity. Apart from these direct effects it is postulated that the compositions of the present invention might also work indirectly by acting as an agent for specific transdermal transport essential metals into the affected joints.

In order to test some of these theories patients aged 18 or over were treated three times daily with either the composition described in Example 2 or a placebo. Neither the patient nor the physician was aware of which agent they received. All patients were assessed to have mild to moderate non-advanced osteoarthritis of hand joints or knee joints will be entered. The patients were assessed before using the composition and two weeks after commencement of treatment. Joint pain was assessed both via palpation, movement and scored by the following scale: 0—Not Tender; 1—Tender; 2—Tender & Winced; 3—Tender, Winced & Withdrew.

Pain, morning stiffness and function were also subjectively assessed by the patient using the 10 cm visual analogue scale.

At the end of the two weeks the patients were asked to assess the composition as to its efficacy, scoring a percentage between 0-100%.

Twenty-two patients completed the trial—three males and nineteen females. The average age was 60, and the distribution of placebo and composition was approximately equal throughout the age range. The degree of severity and joints involved were also similar for the placebo and composition groups. Thirteen patients used the composition from Example 2 and nine used the placebo. The results are shown in Table 6.

TABLE 6

| | Before Treatment (Mean ± SD) | After Treatment (Mean ± SD) |
|---|---|---|
| Treatment Group | | |
| Palpation | 2.53 (0.96) | 0.38 (0.86) * |
| Movement | 1.70 (0.85) | 0.30 (0.85) * |
| Visual Analogue | | |
| Pain | 56.5 (16.8) | 23.4 (22.0) * |
| Morning Stiffness | | |
| Mins | 23.46 (25.85) | 11.69 (22.12) NS |
| Degree | 47.30 (30.83) | 10.76 (27.98) # |

TABLE 6-continued

| | Before Treatment (Mean ± SD) | After Treatment (Mean ± SD) |
|---|---|---|
| Function | 55.38 (20.79) | 25.38 (16.98) * |
| Patient Overall Assessment | | 75% |
| Placebo Group | | |
| Palpation | 2.66 (0.70) | 1.88 (0.95) NS |
| Movement | 2.22 (0.83) | 1.66 (0.95) NS |
| Visual Analogue | | |
| Pain | 54.44 (13.09) | 38.33 (27.27) NS |
| Morning Stiffness | | |
| Mins | 44.44 (57.46) | 17.0 (40.92) NS |
| Degree | 29.44 (30.82) | 19.4 (25.98) NS |
| Function | 66.6 (22.51) | 50.5 (33.35) NS |
| Patient Overall Assessment | | 45% |

Statistical Significance

* = P < .01

# = P < .1

NS Not Significant

This double-blind trial was carried out on patients with clinically well defined osteoarthritis, both placebo and drug treated groups having a similar degree of severity, average age and similar spread of joint involvement. Although the number of patients was not large there was a clear difference between the drug treated and the placebo groups (see Table 6). These differences were shown to be statistically significant to the P<0.01.

The pain score both on palpation and movement was significantly reduced after two weeks of treatment with composition. All measures via the visual analogue scale were also significantly reduced. In contrast none of the parameters measured with the placebo group showed a significant reduction.

When asked to assess the efficacy of the treatment composition, the treated group scored a 75% approval for product, while the placebo group only had a 45% approval rate.

As the only difference between the two compositions was the plasma protein from Example 1, it must be assumed that this product was responsible for the therapeutic effects observed.

Example 5

Topical Treatment in Non-Human Animals

Arthritis is a very common problem in certain dog breeds such as Rottweilers with clinical signs usually becoming evident at about 4-6 months of age.

This trial was therefore conducted on a "double blind" basis to ascertain whether or not the composition described in Example 2 was capable of reliving symptoms.

Twenty-seven dogs were admitted into the trial, twenty-six Rottweilers (including one crossbred Rottweiler) and a Labrador. There was a fairly even distribution of immature and mature dogs and both acute and chronic conditions being treated. A brief summary of the individual results is given in Table 7. The placebo was designated A, while the active agent was designated B.

TABLE 7

| No | BREED | TREATMENT | RESULTS |
|---|---|---|---|
| 1 | Rottweiler | B only | No response and withdrew |
| 2 | Rottweiler | B only | Possible skin reaction to cream and withdrew |
| 3 | Rottweiler | B then A | Some improvement with B, no change with A |
| 4 | Rottweiler | A then B | Improved with A, then worse with B |
| 5 | Rottweiler | A then B | No response to either |
| 6 | Rottweiler | A then B | No response to either |
| 7 | Rottweiler | B only | Lost to follow up |
| 8 | Rottweiler | A then B | No response to either |
| 9 | Rottweiler | B then A | Improved on B, then worse with A |
| 10 | Labrador | B then A | Marked improvement on B, sustained while on A. (NB: older dog with chronic arthritis and both elbows treated) |
| 11 | Rottweiler | A only | No change on A, (both legs) then lost to follow up |
| 12 | Rottweiler | B then A | Improved on B then further on A |
| 13 | Rottweiler | A only | Euthanized after 1 week due to severe hip dysplasia. (Both legs treated) |
| 14 | Rottweiler | B then A | Minimal improvement on B, then further improved on A (Both legs treated) |
| 15 | Rottweiler | A then B | No change with A, slight improvement with but dog was rested |
| 16 | Rottweiler | B then A | Improvement on B, then slipped back again on A. (older dog with chronic arthritis, post surgery) |
| 17 | Rottweiler | B only | Improved in 2-3 days (old post surgery case) Not given A |
| 18 | Rottweiler | B then A | Improved to soundness in 2 days on B. Sesamoid problem developed while on A which did not respond to B treatment. |
| 19 | Rottweiler | B then A | Intermittent lameness improved to soundness on B, and this sustained while on A and for at least 3 months |
| 20 | Rottweiler | A then B | No response, worse on B than A |
| 21 | Rottweiler | B only | Chronic problem in elbows, complicated by sesamoid fragmentation during treatment. B used on L elbow and R sesamoid and dog became sound and has remained so. |
| 22 | Rottweiler | B then A | No response. Very severe case, both legs treated. Dog was destroyed. |
| 23 | Rottweiler | A then B | No response. |
| 24 | Rottweiler | A then B | Slight improvement on A, but then lameness shifted to other leg. No further change on B. |
| 25 | Rottweiler X | B then A | No response. (Chronic post surgery case which was sound until slipped on stairs 4 weeks before entering trial) |
| 26 | Rottweiler | A then B | No change on A - results with B to come |
| 27 | Rottweiler | A then B | Results to come |

The most simple way to examine these results is to assess them on the basis of the "first used" treatment. When this is done, the results are as follows:

|  | TUBE A | TUBE B |
|---|---|---|
| No. of dogs treated | 11 | 15 |
| No of dropouts | 2 | 2 |
| No. completing trial | 9 | 13 |
| No. responding (less lame) | 2 | 10 |
| % RESPONDING | 22.2 | 76.9 |

These results are at first glance better than we expected when we surveyed the combined results of the double-blind study. However, the 77% response rate must be interpreted in the light of a 22% response rate to the placebo (Tube A). Both these results may have been influenced by the weather patterns brought about by running this trial in the Spring. A number of the dog owners suggested that warmer weather at the time of treatment may have been at least in part responsible for the improvement in their dog's lameness. This comment is particularly applicable to Dog 14, which was recorded as a positive response but improved further on Tube A after finishing 2 weeks on Tube B.

Example 6

Evaluation of Inhibitory Activity on Cox-2

Methods employed in this Example have been adapted from the scientific literature to maximize reliability and reproducibility. Reference standards were run as an integral part of each assay to ensure the validity of the results obtained.

Briefly, the COX-2 inhibitory activity was measured by the methods of Riendeau et al., 1997, *Can J Physiol Pharmacol.* 75: 1088-1095 and Warner et al., 1999, *Proc Nati Acad Sci USA* 96 (13): 7563-7568. Cyclooxygenase-2 source was human recombinant insect Sf21 cells. The substrate was 0.3 µM arachidonic acid in the vehicle of 1% DMSO. The pre-incubation time was 15 minutes at 37° C., while the incubation time was 5 minutes at 37° C. The incubation buffer was 100 mM Tris-HCl, pH 7.7, 1 mM glutathione, 1 µM Hematin, 500 µM phenol. The quantitation Method was EIA quantitation of $PGE_2$, with a significance criteria of 50% of max stimulation or inhibition.

The biochemical assay results are presented as the percent inhibition of specific binding or activity. For primary assays, only the lowest concentration with a significant response judged by the assays' criteria is shown. Where applicable, either the secondary assay results with the lowest dose/concentration meeting the significance criteria or, if inactive, the highest dose/concentration that did not meet the significance criteria is shown. Primary screening was conducted in duplicate with quantitative data e.g., $IC_{50}\pm SEM$, $Ki\pm SEM$ and nH) are shown where applicable for individual assays. In screening packages, primary screening in duplicate with semi-quantitative data (e.g., estimated $IC_{50}$, Ki and nH) are shown where applicable (concentration range of 4 log units); available secondary functional assays are carried out (30 µM) and MEC or MIC determined only if active in primary assays >50% at 1 log unit below initial test concentration.

Significant responses (≧50% inhibition or stimulation for Biochemical assays) were noted in the primary assays.

Table 8 shows the primary test for COX-2, while Table 9 shows the experimental results.

TABLE 8

| Biochemical Assay | Species | Conc. | % Inhibition |
|---|---|---|---|
| COX-2 | Human | 10% | 84 |

TABLE 9

| Test | Target | Species | Conc. | % Inhibition | $IC_{50}$ |
|---|---|---|---|---|---|
| 1 | COX-2 | Human | 10% | 84 | |
| 2 | COX-2 | Human | 1% | 70 | |
| 3 | COX-2 | Human | 10% | 92 | 0.679% |
| 4 | COX-2 | Human | 0.1% | 5 | |
| 5 | COX-2 | Human | 0.01% | 3 | |

Figure 2:
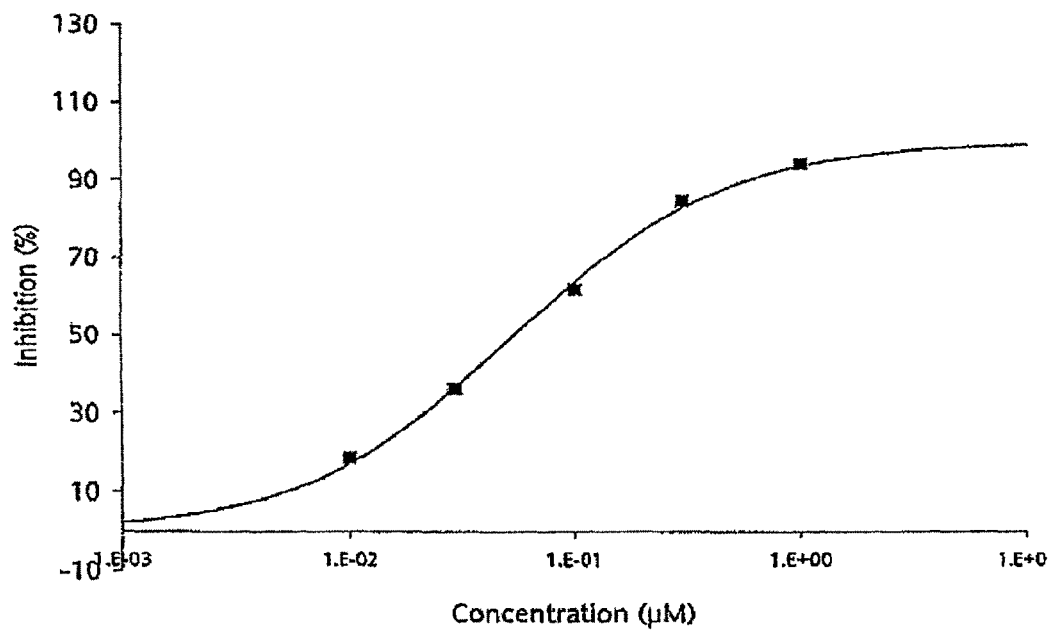
FIG. 2 shows a dose response curve for % inhibition of COX-2 activity by a reference COX-2 inhibitor, i.e. rofecoxib.

In both assays the reference compound was Rofecoxib with an historical $IC_{50}$ of 0.17 μM and concurrent $IC_{50}$ of 0.0992 μM. These results are shown pictorially in FIGS. 1 and 2.

Example 7

Preparation of Analgesic and Anti-Inflammatory Composition

An analgesic and anti-inflammatory composition was produced by the method outlined in Example 1. Basically, eighty liters of isolated plasma was mixed and incubated for 4 hours in the presence of 1% sodium bicarbonate ($NaHCO_3$). The plasma protein was then heated to not higher than 80° C. and allowed to precipitate. The resulting curd was filtered out, and allowed to air dry at 80° C. to a moisture level of 10%. Fifty gram of the dried soluble protein was added to water to reach a 1 liter volume. The protein and water were heated to 80° C. for 1 hour during which stage the protein dissolved. This mixture was cooled to 40° C. The temperature was maintained between 35-39° C. while adding 0.125 gram of trypsin powder. This was stirred for 1.5 hours to produce a denatured plasma protein solution.

Figure 3:
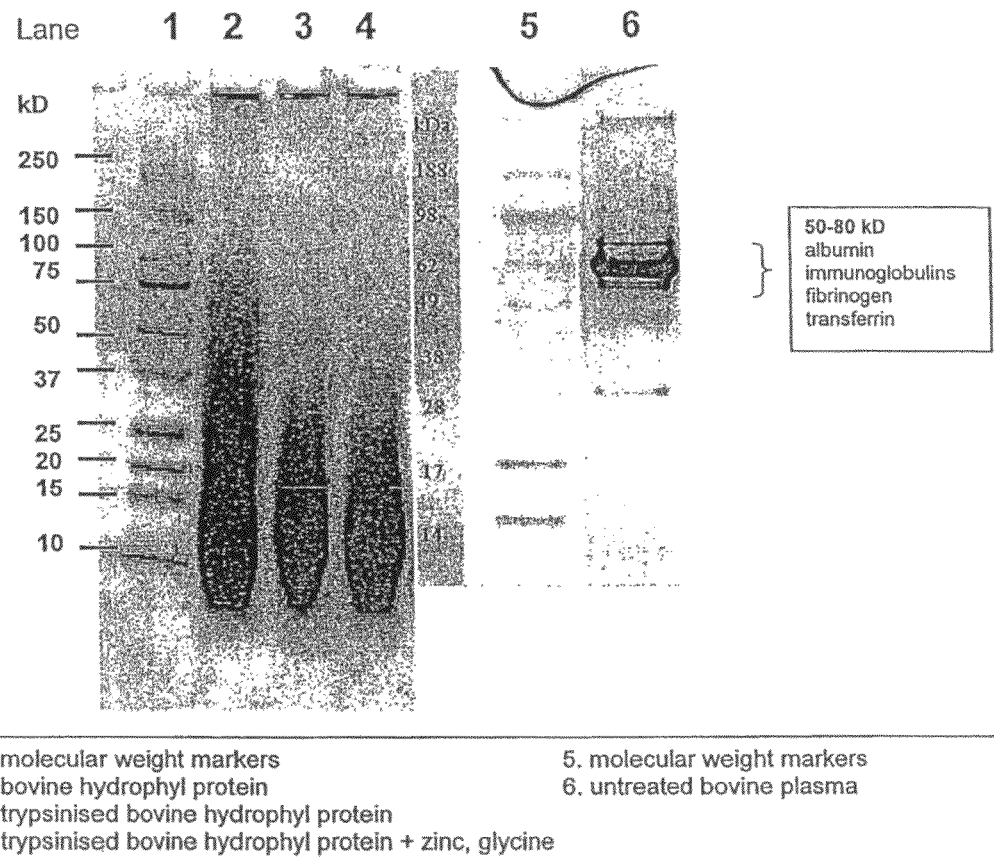
FIG. 3 (left panel) shows a 10-20% SDS-PAGE Tricine gradient gel. Proteins were stained with Coomassie blue. Lane 1 contains molecular weight markers. Lanes 2 shows bovine soluble protein prior to trypsinisation and lane 3 and 4 after trypsinisation, as indicated. This gel shows that the majority of proteins with aromatic rings in the preparation are in a size range less than 50 kilodaltons.
Figure 4:
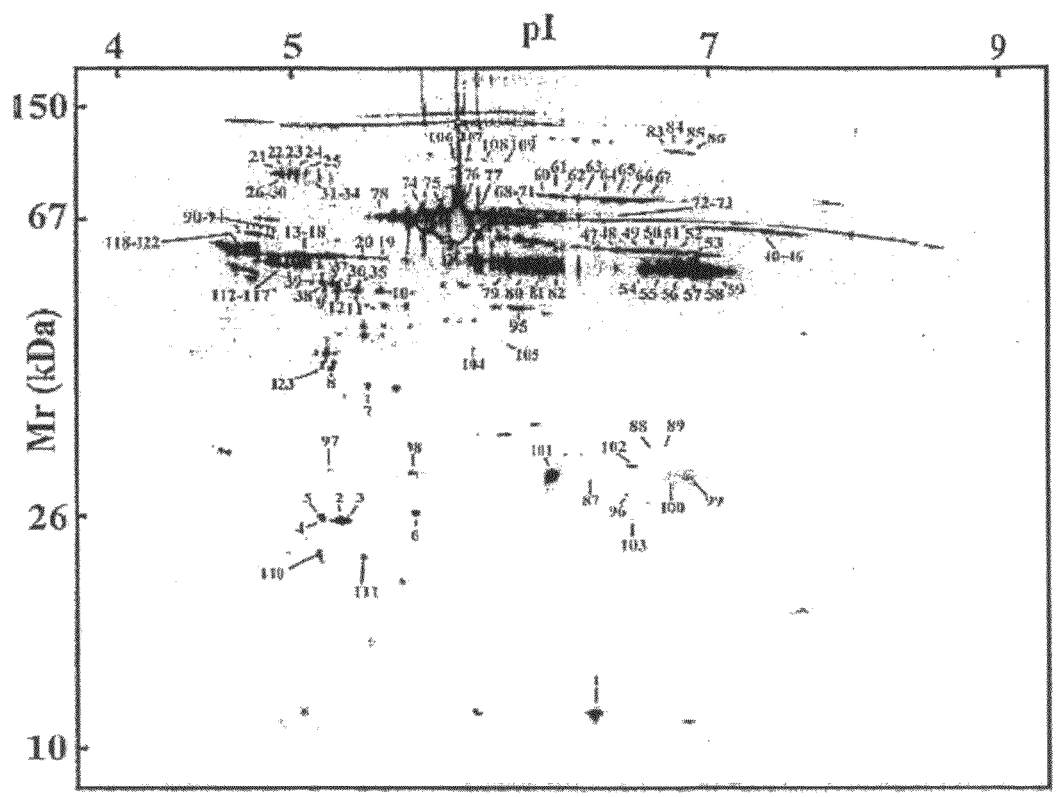
FIG. 4 shows bovine plasma by 2-D electrophoresis map using the method of Talamo et al., 2003, *Proteomics,* 3:440-460.
Figure 5:
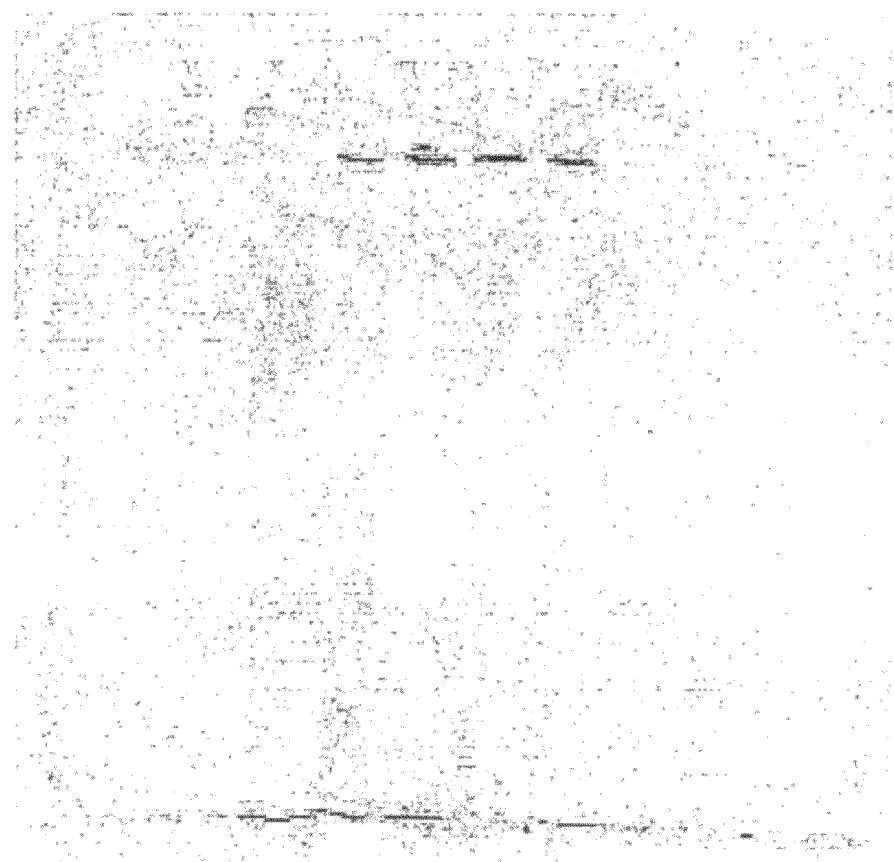
FIG. 5 shows an 8% SDS-PAGE Tris-glycine gel. Lanes are as in the left section of FIG. 1. This gel confirms that the majority of proteins with aromatic rings in the preparation are in a size range less than 50 kilodaltons.

FIGS. 3 to 5 show the soluble plasma protein fragments obtained by this method. In FIG. 3, the major protein bands apparent in untreated plasma separated by SDS-PAGE are 50-80 kDa in size (Lane 6) Proteomic analysis of these bands identified them as consisting mainly of albumin, immunoglobulins, fibrinogen and transferrin (FIG. 4).

In contrast, the plasma protein before protease treatment consists mainly of polypeptides smaller than 50 kDa (FIG. 3. Lane 2), while after trypsinisation the soluble plasma protein fragments are reduced to molecular weights of less than 25 kDa (10-20% tricine gradient gel, FIG. 3. Lanes 3, 4). FIG. 5 shows the same samples on an 8% trisglycine gel.

Example 8

Cox-2 Inhibition

Cyclooxygenase is the key enzyme in the synthesis of prostaglandins from arachidonic acid. In 1991, several laboratories identified a product from a second gene with Cox activity and called it Cox-2. Cox-1 is widely distributed in the body's cells, from the stomach to the platelets of the blood. Continuously present in the body, they serve "housekeeping" functions that maintain various normal physiological conditions. Cox-2 is induced by inflammatory and other injurious stimuli, and they tend to localize in the sites of injury, for instance the swelled joints of people suffering from rheumatoid arthritis. PGE2 has also been reported to enhance sensitization at the spinal cord resulting in hyperexcitability. Protective prostaglandins, which preserve the integrity of the stomach lining and maintain normal renal function in a compromised kidney, are synthesized by Cox-1. Gastrointestinal side effects of COX inhibitors are blamed for roughly 100,000 hospitalizations and 15,000 deaths each year in the United States alone. Therefore Cox-2 inhibitors, like Celebrex and Vioxx rapidly overhauled the non-selective Cox-inhibitory, like aspirin. However in late 2004, a major trial on long term treatment found that almost twice the subjects who took Vioxx for eighteen months had strokes or heart attacks than subjects on placebo. Vioxx was immediately withdrawn from the market. The strategy of using selective Cox-2 inhibitors is being reassessed. Most likely patients will benefit most when the treatment regime of non-selective Cox or Cox-2 inhibitors is taking into consideration possible Cox-inhibition sensitivities, treatment duration and route of application.

Figure 6:
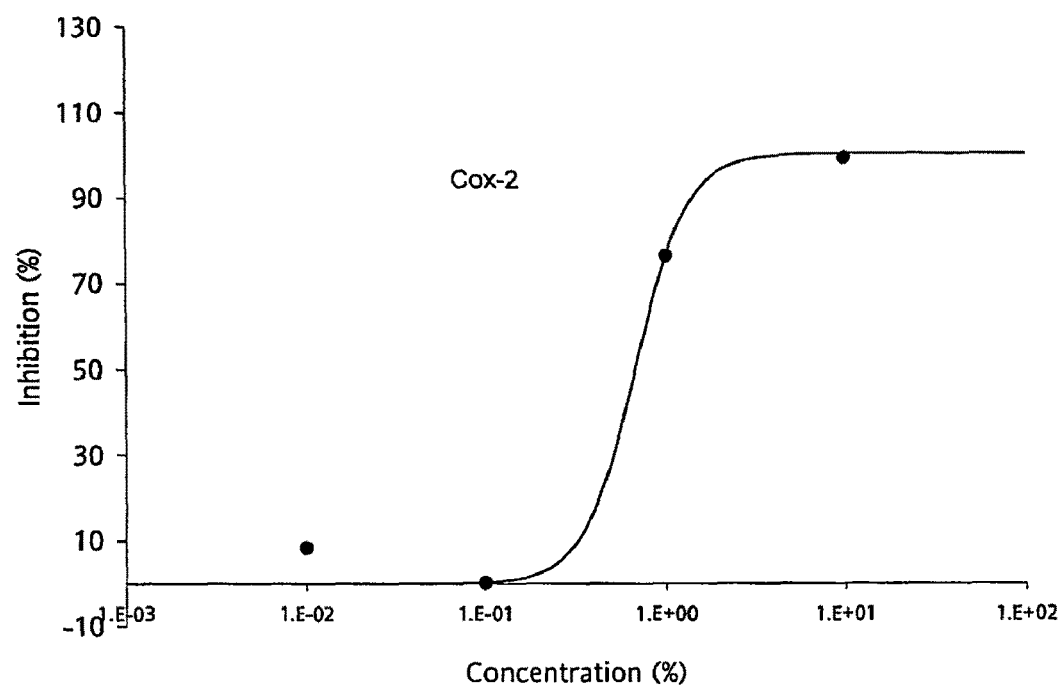
FIG. 6 shows inhibition of COX2 in human recombinant insect sf21 cells in vitro with the composition of the present invention comprising zinc chloride, glycine and trypsinised protein ($IC_{50}$ of 0.68% of the test composition). COX2 inhibition is a known mechanism through which clinical inflammatory pain is reduced.

As shown in FIG. 6, the soluble plasma test composition was found to inhibit the human platelet Cyclooxygenase-2 (Cox-2) with an $IC_{50}$ of 0.68% of the soluble plasma test composition solution.

The soluble plasma test composition inhibited the binding of [$^3$H] Prostaglandin E2 (PGE2) to its receptor on human recombinant HEK-293 cells with a Ki of 0.89% ($IC_{50}$=2.0%) of the soluble plasma test composition solution. By inhibiting PGE2 to bind to the EP2 receptor, the test composition indirectly inhibits COX2.

Table 10 shows the targets and the effects shown by the soluble plasma test composition of the present invention.

TABLE 10

| Target | Effect | Effect of 10% test composition | $K_i$ | $IC_{50}$ |
|---|---|---|---|---|
| Cox-2 | Inhibition | 92% | | 0.7% |
| $PGE_2$ receptor | Binding | 84% | 0.9% | 2.0% |

Table 11 shows the biochemical mechanisms that are associated with examples of different diseases and conditions.

TABLE 11

| Indication | Mechanism |
|---|---|
| Arthritis | COX inhibition |
| | $PGE_2$ receptor antagonism |
| Muscular pain | $PGE_2$ antagonism |
| | COX inhibition |
| Actinic skin keratosis | COX inhibition |
| | PGE2 antagonism |
| Inflammatory pain | COX inhibition |
| | PGE2 antagonism |
| Ankylosing spondylitis | COX inhibition |
| | PGE2 antagonism |
| Lupus | |
| Crohn's disease | |
| Post-operative pain | $PGE_2$ antagonism |
| | COX inhibition |
| Repetitive strain injury (sports related) | COX inhibition |
| | PGE2 antagonism |

The claims defining the invention are as follows:

1. A method for inhibiting COX-2 activity, said method comprising contacting a cell expressing COX-2 with an effective amount of a COX-2 inhibitor comprising a mixture of denatured plasma proteins and at least one metal ion or metal salt thereof, wherein the COX-2 inhibitor is manufactured by:
   (a) mixing plasma with sodium bicarbonate ($NaHCO_3$) and trypsin incubating said mixture for sufficient time and at a temperature of no more than 80° C. to produce a precipitate of denatured plasma proteins;
   (b) resolubilising said precipitate in the presence of an aqueous solution at a temperature of between about 80° C. and about 150° C., wherein either before, during or after the resolubilising step at least one metal ion or metal salt thereof is admixed; and
   (c) separating the COX-2 inhibitor from the resolubilised precipitate in step (b), which COX-2 inhibitor comprises denatured plasma proteins and the at least one metal ion or metal salt thereof.

2. The method of claim 1, wherein the denatured plasma proteins in the COX-2 inhibitor in step (c) comprises soluble plasma proteins consisting essentially of protein or protein fragments having molecular weights less than 50 kDa as determined by SDS-PAGE.

3. The method of claim 1, wherein the plasma is isolated from an animal selected from the group consisting of a human, an equine, a bovine, an ovine, a murine, a caprine and a canine.

4. The method of claim 1, wherein the step of separating the COX-2 inhibitor is by chromatography.

5. The method of claim 1, wherein the metal ion is selected from the group consisting of nickel, sodium, copper, zinc, cobalt, iron, magnesium, manganese, potassium, silver and mercury, ions or salts thereof and mixtures thereof.

6. The method of claim 1, wherein the metal ion is a mixture of metals consisting essentially of $NiSO_4.7H_2O$, $NH_4VO_3$, $NaF$, $CuSO_4.5H_2O$, $ZnCl_2$, $(NH_4)_6Mo_7O_{24}.4H_2O$, $CoCl_2.6H_2O$, $FeSO_4.7H_2O$, $MgSO_4.7H_2O$, $H_3BO_3$, $MnCl_2.4H_2O$ and $K_2CrO_4$.

7. The method of claim 1, wherein the COX-2 inhibitor is admixed with a pharmaceutical carrier.

8. The method of claim 1, wherein the step of contacting a cell expressing COX-2 is in vitro.

9. The method of claim 1, wherein the step of contacting a cell expressing COX-2 is in vivo.

10. A method for inhibiting COX-2 activity, said method comprising contacting a cell expressing COX-2 with an effective amount of a COX-2 inhibitor comprising a mixture of denatured plasma proteins and at least one metal ion or metal salt thereof, wherein the COX-2 inhibitor is manufactured by:
    (a) mixing plasma with sodium bicarbonate ($NaHCO_3$) and incubating said mixture for sufficient time and at a temperature of no more than 80° C. to produce a precipitate of denatured plasma proteins;
    (b) resolubilising said precipitate in the presence of an aqueous solution and trypsin at a temperature of between about 80° C. and about 150° C.; wherein either before or during the resolubilising step at least one metal ion or metal salt thereof is admixed; and
    (c) separating the COX-2 inhibitor from the resolubilised precipitate in step (b), which COX-2 inhibitor comprises denatured plasma proteins and the at least one metal ion or metal salt thereof.

11. The method of claim 10, wherein the plasma is isolated from an animal selected from the group consisting of a human, an equine, a bovine, an ovine, a murine, a caprine and a canine.

12. The method of claim 10, wherein the step of separating the COX-2 inhibitor is by chromatography.

13. The method of claim 10, wherein the metal ion is selected from the group consisting of nickel, sodium, copper, zinc, cobalt, iron, magnesium, manganese, potassium, silver and mercury, ions or salts thereof and mixtures thereof.

14. The method of claim 10, wherein the metal ion is a mixture of metals consisting essentially of $NiSO_4.7H_2O$, $NH_4VO_3$, $NaF$, $CuSO_4.5H_2O$, $ZnCl_2$, $(NH_4)_6Mo_7O_{24}.4H_2O$, $CoCl_2.6H_2O$, $FeSO_4.7H_2O$, $MgSO_4.7H_2O$, $H_3BO_3$, $MnCl_2.4H_2O$ and $K_2CrO_4$.

15. The method of claim 10, wherein the COX-2 inhibitor is admixed with a pharmaceutical carrier.

16. The method of claim 10, wherein the step of contacting a cell expressing COX-2 is in vitro.

17. The method of claim 10, wherein the step of contacting a cell expressing COX-2 is in vivo.

18. The method of claim 10, wherein the method inhibits COX-2 activity by inhibiting prostaglandin E2 binding to receptor EP2.

19. The method of claim 1, wherein the method inhibits COX-2 activity by inhibiting prostaglandin E2 binding to receptor EP2.

* * * * *

UNITED STATES PATENT AND TRADEMARK OFFICE
CERTIFICATE OF CORRECTION

| | | |
|---|---|---|
| PATENT NO. | : 8,236,355 B2 | Page 1 of 1 |
| APPLICATION NO. | : 12/226786 | |
| DATED | : August 7, 2012 | |
| INVENTOR(S) | : Maud Louisa Johanna Maria Eijkenboom | |

It is certified that error appears in the above-identified patent and that said Letters Patent is hereby corrected as shown below:

On the Title Page, item [75] should read as follows:

[76] "Maud Louisa Johanna Maria Eijkenboom", Melville (AU)

Signed and Sealed this

Eighth Day of October, 2013

Teresa Stanek Rea
*Deputy Director of the United States Patent and Trademark Office*